United States Patent [19]

De Ambrosi et al.

[11] Patent Number: 4,746,730

[45] Date of Patent: May 24, 1988

[54] BIO-AVAILABLE IRON-PROTEIN DERIVATIVES AND PROCESS FOR THEIR PREPARATION

[75] Inventors: Luigi De Ambrosi, Santhià; Piergiuseppe Pagella, Alessandria, both of Italy

[73] Assignee: Mediolanum Farmaceutici, Milan, Italy

[21] Appl. No.: 74,862

[22] Filed: Jul. 17, 1987

Related U.S. Application Data

[63] Continuation-in-part of Ser. No. 927,450, Nov. 6, 1986, abandoned.

[30] Foreign Application Priority Data

Nov. 6, 1985 [IT] Italy ............................ 22730 A/85

[51] Int. Cl.$^4$ ...................... C07K 13/00; A61K 37/14
[52] U.S. Cl. .................................. 530/385; 530/400; 530/402; 530/410
[58] Field of Search ............... 530/385, 400, 402, 410; 514/6

[56] References Cited

U.S. PATENT DOCUMENTS

| | | | |
|---|---|---|---|
| 4,411,915 | 10/1983 | Eriksson ...................... | 530/385 X |
| 4,493,829 | 1/1985 | Sportoletti et al. ............ | 530/400 X |
| 4,518,525 | 5/1985 | Autio et al. .................. | 530/385 |
| 4,610,814 | 9/1986 | Dede et al. .................. | 530/385 X |

*Primary Examiner*—Howard E. Schain
*Attorney, Agent, or Firm*—Stevens, Davis, Miller & Mosher

[57] ABSTRACT

Bio-available iron-protein derivatives having an iron content of from 2% to 20% by weight and a nitrogen content of from 12% to 16% by weight obtained by reacting acetylated globin with an iron compound selected from the group consisting of ferric chloride, iron fructate and iron saccharate, and pharmaceutical compositions for treating and preventing iron deficiency in animals and humans.

10 Claims, No Drawings

BIO-AVAILABLE IRON-PROTEIN DERIVATIVES AND PROCESS FOR THEIR PREPARATION

This application is a continuation-in-part of application Ser. No. 927,450, filed Nov. 6, 1986, now abandoned.

The present invention relates to a new class of iron-protein derivatives obtained by the reaction between acetylated globin, prepared from red blood cells of animal origin, and inorganic or organic iron compounds. The iron protein derivatives of the invention contain a high percentage of complexed iron.

They show an excellent bio-availability and are useful for the oral treatment of iron deficiency anaemia.

Some iron protein derivates are known in the art as for example those described in U.S. Pat. Nos. 4,411,915, 4,493,829 and 4,610,814.

These derivatives include a heme-iron-enriched fraction prepared with the aid of proteolytic enzymes which hydrolyze the globin of the original heme protein to amminoacids of lower molecular weight, or the succinylated derivatives of many animal or vegetable proteins with an effective iron content in the range of 0.4-8.4% by weight, or the reaction products of plasma protein and haemoglobin with a mixture of inorganic salts.

None of the known processes uses protein acetylation to produce iron protein derivates.

We now have found that the acetylated globin is very soluble in water at the pH range of 6 to 8, i.e. the pH range present in the intestinal tract, the place assigned to the iron absorption.

In this respect, the acetylated globin behaves very differently from globin, which is very soluble in water at pH values lower than 5, but is scarcely soluble in the pH range between 6 and 8, as reported by Autio K. et al. Journal of Food Science (1984), 49, pag. 859.

The solubility of acetylated globin at the intestinal values of pH is very important when the protein is used as a iron carrier because it favors its intestinal absorption.

These findings, together with the well known ability of globin to prevent the formation of poorly absorbed iron polymers (W. Forth and W. Rummel, Phys. Rev. 1973, 53, 724) which is retained by acetylated globin, and with the high percentage of iron vehiculated by the proteic carrier, make the compounds of this invention very useful for the oral treatment of iron deficiency anaemia.

The present invention relates to a new class of iron protein derivates containing a high percentage of absorbable iron, which are stable and very soluble. They increase, when orally administered to experimental animals, basal values of sideremia and they show a therapeutic effect on experimental anaemia when administered orally at very low dosages. Moreover they do not cause gastrointestinal damages.

The present invention therefore relates to iron protein derivatives characterised in that they contain an amount of complexed iron of from 2% to 20% by weight and have a nitrogen content of from 12 to 16% by weight and are obtained by reacting acetylated globin with an iron compound.

These derivatives are useful as an active principle in the preparation of pharmaceutical compositions for treating and preventing iron deficiency anaemia, both for human or animal use.

The invention also relates to a process for the preparation of said iron protein derivatives which comprises:
(a) separating globin from the animal red blood cells by the acidified acetone method;
(b) purifying globin by dissolving it in water and by ultrafiltering the aqueous solution;
(c) concentrating the aqueous solution up to a globin content of from 2.5 to 10% by weight;
(d) adding acetic anhydride to the aqueous solution of globin, while maintaining the pH of the reaction mixture at a value of from 8 to 9 by means of an aqueous N/10 solution of NaOH, until the desired acetylation degree of from 10% to 100% is reached;
(e) purifying the acetylated globin by acid precipitation, filtration and redissolution in alkaline water up to an acetylated globin content of from 2.5 to 10% by weight;
(f) reacting the purified acetylated globin with an aqueous solution of an iron compound selected from the group consisting of ferric chloride, iron fructose and iron saccharate for a time of from 1 to 3 hours and at room temperature;
(g) purifying the reaction product by acid precipitation and alkaline redissolution;
(h) recovering the product by lyophilizing the obtained aqueous solution.

Globin may be obtained through many methods, such as e.g. acidified acetone, hydrogen peroxide, proteolytic enzyme, carboxymethylcellulose [Rosis Fanelli A., Antonini E., Caputo A. (1958) Biochim. Biophys. Acta, 30, 608] [Wismer-Pedersen J. (1980) Fleichwirtsch 60, 987] [Eriksson C. (1978) In Biochemical Aspects of New Protein Food 44, pag. 43, Ed. Adler-Nissen, J. Eggum, B.O., Munck L. and Olsen H. S.] [Autio K., Kiesvaara, Mälkki Y., Kanko S. (1984) J. Food Sci. 49, 859].

According to the present invention globin is preferably prepared from animal red blood cells using acidified acetone.

The obtained Globin is brought to a pH of 9,5–10,5 by adding a solution of N/10 NaOH.

Acetic anidride and a solution of N/10 NaOH are slowly added simultaneously so as to keep the pH at values varying from 7,5 to 8,5.

The mixture is filtered and acidified with a 5N HCl solution to pH 3–3,5.

The precipitate thus obtained is separated by filtration, suspended in distilled water and dissolved again adding NaOH to pH 7,5–8,5. The reaction mixture thus obtained is filtered and the purification treatment (precipitation, filtration, dissolution) is repeated, then the purified mixture is filtered or dialyzed and lyophilized. The lyophilizate consists of acetylated globin, the level of acetylation depending on the quantity of acetic anhydride used. The preferred acetylation degree is of from 10 to 100% of the amine groups content of globin.

The iron protein derivative is obtained by reacting the obtained acetylated globin with an aqueous solution of an iron compound selected from the group consisting of ferric chloride, iron saccharate and iron fructate.

The iron saccharate and iron fructate are obtained by reacting at room temperature and in alkaline conditions an aqueous solution of sucrose or fructose with ferric chloride.

The weight ratio between iron and sucrose or fructose in the reaction mixture is of from 1:5 to 1:20.

The obtained iron saccharate or fructate has an iron content of 10% by weight.

The acetylated globin is dissolved in distilled water and an aqueous solution of iron-fructate or saccharate prepared as above is added slowly at room temperature. The ratio, by weight, between acetylated globin and iron varies from 19:1 to 4:1.

The acetylated globin solution has preferably a concentration which varies between 2,5% and 10%, while the iron fructate or saccharate has preferably a concentration which varies between 5% and 10% by weight.

The mixture is kept stirred for 1-3 hours and then is slowly treated with 0,1N HCl until the value of pH is reduced from 7 to 5, a precipitate being thus obtained.

The precipitate is separated by filtration or centrifugation, washed with a dilute solution of HCl, suspended in distilled water and dissolved again by slowly adding a 1N NaOH solution until pH 7.

The clear mixture is dialyzed or ultrafiltered and, at the end, lyophilized.

The iron protein derivative thus formed, consisting of iron acetylated globin, has a iron content which can vary from 5 to 20% by weight, a content of proteic nitrogen in the range of from 15.6 to 12.8% by weight and a water solubility of 30% weight/volume.

As an alternative to the process already described, the acetylated globin solution is reacted with a solution of an inorganic iron salt, preferably $FeCl_3 \cdot 6H_2O$, with a ratio by weight between acetylated globin and iron from 49:1 to 15:1, at room temperature, under stirring for 10-60 minutes. The inorganic iron salt solution has, preferably, a concentration which can vary from 2,5 to 10% by weight.

A precipitate is formed and it is treated as described above.

The final product, obtained by lyophilisation, consists of iron acetylated globin and has a content of complexed iron of from 2 to 6% by weight; a content of proteic Nitrogen of from 15 to 16% by weight and a solubility in water equal to 30% weight/volume.

The ccompounds obtained by reaction with $FeCl_3 \cdot 6H_2O$ have a noticeably lower iron content than the compounds obtained by reaction with iron fructate or saccharate; nevertheless both kinds of products find their specific therapeutical use. The iron contained in the products of the present invention is completely complexed as demonstrated by precipitation with ammonium sulphate and with N/10 HCl and as shown by the complete solubility in an alkaline medium, a condition in which the iron ion precipitates.

The test of precipitation with ammonium sulphate is carried out by adding to a 10% solution of the iron protein derivative 30% (w/v) of ammonium sulphate.

The precipitate thus obtained is exactly similar to the previous iron protein derivative, which is again soluble in alkaline medium, whereas there is no free iron in solution. The compounds obtained, as described above, are stable in acid medium and have a good solubility in water and in alkaline medium. They are particularly soluble at values of pH present in the intestine, where complexed iron is quickly released after having been orally administered, thus increasing the values of the basal sideremia without causing any damage to the gastrointestinal system. The present invention also refers to pharmaceutical formulations (vials, tablets, capsules, syrups, small envelopes with granulate etc.), which contain an effective amount of iron protein derivatives as active principle and are useful for the treatment and prevention of iron deficiency anaemia.

The following preferred formulations are mentioned as examples and do not have to be considered limiting the invention:

Vials containing 10-20-40-100 mg of iron as iron protein derivatives and besides aqueous solvent, flavourings, stabilizers, and usual pharmaceutically acceptable additives;

Tablets containing 10-20-40-100 mg of iron as iron protein derivatives and besides excipients, disgregating elements, and the usual pharmaceutically acceptable additives;

Capsules containing 10-20-40-100 mg of iron as iron protein derivatives separation plugs containing 10-20-40-100 mg of iron as protein derivatives inserted in large phials contaning suitable solvents;

Small monodose envelopes contaning a granulate with 10-20-40-100 mg of iron as protein derivatives;

Syrups containing 1-2-4-10 mg/ml of iron as iron protein derivatives and besides aqueous solvent, flavorings, stabilizings, and usual pharmaceutically acceptable additives.

The following examples are reported to the purpose of illustrating without limiting the invention.

EXAMPLE 1

(a) Globin preparation starting from red blood cells 500 ml of bovine citrate blood are centrifugated at 3000 rpm. The corpuscolar mass washed twice in a volume of 300 ml of saline solution is dissolved in a volume of 800 ml of acetone at 5° C. and 100 ml of a solution of conc. HCl and acetone (1:10) is added. The proteic suspension thus obtained is kept at a low temperature (5° C.) for 12 hours thus facilitating the globin precipitation.

The precipitate is separated by centrifugation, dried and pulverized. The obtained globin (60 g) is purified by dissolution in 5 liters of water at 40° C. followed by a filtration through paper till it becomes clear and then by a ultrafiltration at 10000 cut off. 50 g of purified globin in solution 2.5% are finally obtained by concentrating.

(b) Preparation of acetylated globin

An amount of 400 ml of compound (a) (10 g of globin) are slowly made alkaline with 1N NaOH to pH 10 under stirring. Then 5 ml of acetic anhydride and at the same time 1N NaOH, to keep the mixture at a pH of about 8, are added. When the addition is ended the reaction mixture is kept under stirring for 60 min. at room temperature.

The opalescent solution is filtered off until it becomes clear, then it is slowly made acid with 5N HCl till pH 3-3.5.

The precipitate being formed is filtered off, suspended in 100 ml of $H_2O$ and 1N NaOH is added till complete dissolution (pH about 8). The mixture is filtered off again and then made acid with HCl till pH 3-3.5.

The precipitate being formed is filtered off, suspended in 100 ml of $H_2O$ and dissolved again by addition of 1N NaOH to pH 8.

The clear mixture is dialyzed or ultrafiltered and then lyophilized.

The lyophilizate obtained consists of 7 g of acetylated globin, whose level of acetylation corresponds to 95%.

The acetylation level is given by the ratio between the percentage of acetylated groups and the groups of the previous globin which are not yet acetylated and it is determined by ninidrine reaction of the free amminic groups (J. Biol. Chem. 211, 1954, 907).

(c) Preparation of saccharate iron and fructate iron

In the preparation of iron fructate an amount of 50 g of iron chloride hexahydrate is dissolved in 2 liters distilled water and added slowly to 500 ml of a mixture containing 300 g fructose.

After having mixed the compounds the pH is slowly brought to 7.8–8.5 by adding a solution of KOH at 20%. The mixture is kept under stirring for many hours, the pH being maintained at 8–8.5.

When the pH is stable, the solution is filtered and then diluted in water 1:100 and filtered at 1000 cut off with continual addition of distilled water till negative reaction of ferric iron in the permeate.

The solution is concentrated to about 800 ml, then filtered and lyophilized. Yield=80 g of powder, iron content=10%.

In the preparation of saccharate iron 50 g of iron chloride hexahydrate are dissolved in 2 liters of distilled water and are slowly poured in 1 liter of a solution containing 500 g of saccharose.

After mixing, the pH is brought slowly to 8.0–8.5 by means of a 20% solution of methylglucamine. The mixture is stirred for many hours taking the pH back at its previous values by addition of methylglucamine solution. When the solution is stable, it is heated at 50° C. for about 30 min. and filtered. The mixture is diluted to 5 liters with water and it is ultrafiltered at a cut-off of 1000 with continuous addition of distilled water till negative ferric iron reaction in the permeate. The solution is concentrated to 500 ml, filtered and lyophilized. Yield: 50 g of powder with an iron content of 10%.

(d) Preparation of iron acetylated globin by means of saccharate iron.

3 g of acetylated globin, obtained as described above in phase (b), are dissolved in 60 ml of $H_2O$ (pH about 7.5), and 6 g of saccharate iron (10% iron) prepared as described in phase (c) and dissolved in 6 ml $H_2O$ are slowly added under stirring.

When the addition is ended the reaction is allowed to proceed for 2 hours under stirring at room temperature.

The obtained mixture is slowly acidified with 0.1N HCl till it precipitates to pH 5.

The precipitate is filtered off, washed with 30 ml of 0.01N HCl, suspended in 30 ml of $H_2O$ and dissolved again by adding slowly N1 NaOH till pH 7.

The clear mixture is then ultrafiltered or dyalized and lyophilized. The solid obtained by lyophilization (2.7 g) has a content of complex iron corresponding to 14.1%, a solubility in water of 30% weight/volume a protein nitrogen content of 12.8%.

EXAMPLE 2

Preparation of iron acetylated globin by means of iron-fructate

With the same modalities described in the first example an iron protein derivative is obtained starting from 3 g of acetylated globin and from 6 g of fructate iron (iron=10%) prepared as described in phase (c) of the first example.

The solid obtained by lyophilization has an iron content of 12.4%, a solubility in water of 30% weight/volume and a proteic nitrogen content of 14% by weight.

EXAMPLE 3

Preparation of iron acetylated globin by means of iron chloride

An amount of 1 g of acetylated globin, obtained as described in phase (b) of the first example, is dissolved in 10 ml of water (pH 7) and added to 0.83 g of iron chloride dissolved in 10 ml of $H_2O$ (pH 2). The mixture is kept stirred for about 30 minutes. The formed precipitate is filtered off, washed with 30 ml 0.01N HCl and dissolved again by slowly adding 1N NaOH till pH 7.5. The mixture is filtered off, dyalized and lyophilized. The solid obtained by lyophilization has a iron content of 4.5%, a water solubility of 30% weight/volume and a protein nitrogen content of 15% by weight.

TOXICITY

The acute toxicity has been evaluated on mice after an oral administration of iron-derivatives according to the invention, and a DL50 has been found that is in any case higher than 4000 mg/kg.

On the contrary ferrous sulphate, after an oral administration has in mice a DL50 which corresponds to 1500 mg/Kg.

Sideremia after oral administration

The capacity of the iron derivatives of the present invention to increase the basal values of sideremia has been evaluated in 180–200 g rats S.D. which had been fasting for 18 hours. The products were administered by gastric probe two hours before the sacrifice of animals, with doses containing a quantity of iron equal to 2 mg/kg.

The determination of the quantity of iron in serum has been carried out by a spectrophotometer with a betaphenantroline method (colorimetric method, Boehringer Mannheim). The results are reported in Table I.

TABLE I

| Treatment | Iron in the serum μg/100 ml |
| --- | --- |
| Saline | 150 ± 20.4 |
| Compound of Example 1 | 322 ± 6.4 |
| Ferrous sulphate | 269 ± 36.7 |

Therapeutic activity of Example 1 compound on anaemia induced in the growing rat by repeated bleeding and feeding a low iron diet Anaemia in rats was induced as previously described (P. G. Pagella et al; 1984, Arzn. Forsc. 34, 952). Group of male rats weighing 40–50 g were given (day 0) the low iron diet (containing <1 mg iron/kg diet) and distilled water ad libitum for the duration of experiment. After 21 and 28 days the rats were bled by cardiac puncture 2 ml/rat each time, the rats were divided into homogeneous groups on the basis of hemoglobin values observed at the 2nd cardiac puncture.

The compound of Example 1 was orally administered, in amount corresponding to 1 mg/kg/die as iron from 35 day to the end of experiment. The hemoglobin values were evaluated, at 7th–14th–21st day of drug treatment, on blood samples withdrawn by tail cut. At the end of experiment the rats were sacrificed and the stomachs were removed and observed.

The results are shown in Table 2 and show the potent anti-anaemic effect of the compound of exp. 1. No gastric lesion were observed in drug treated rats.

TABLE 2

| Iron mg/kg/die | hemoglobin (g %) treatment day | | |
|---|---|---|---|
| | 7 | 14 | 21 |
| 0 | 6.26 ± 0.21 | 6.12 ± 0.28 | 5.98 ± 0.30 |
| 1 | 8.34 ± 0.23 | 10.04 ± 0.14 | 12.72 ± 0.22 |

We claim:

1. Bio-available iron-protein derivatives having an iron content of from 2% to 20% by weight and a nitrogen content of from 12% to 16% by weight obtained by reacting acetylated globin with an iron compound selected from the group consisting of ferric chloride, iron fructate and iron saccharate.

2. Bio-available iron-protein derivatives according to claim 1 in which the globin is extracted from animal red blood cells.

3. Bio-available iron-protein derivatives according to claim 1 in which acetylated globin has an acetylation grade of from 10% to 100% by weight.

4. A process for the preparation of bio-available iron-protein derivatives having an iron content of from 2 to 20% by weight and a nitrogen content of from 12 to 16% by weight which cmoprises:

(a) separating the globin from animal red blood cells by the acidified acetone method;

(b) purifying the globin by dissolving it in water and by ultrafiltering the aqueous solution;

(c) concentrating the aqueous solution up to a globin content of from 2,5% to 10% by weight;

(d) adding to the aqueous solution of globin acetic anhydride, while maintaining the pH of the reaction mixture at a value of from 8 to 9 by means of N/10 NaOH, until the desired acetylation degree of from 10% to 100% is reached;

(e) purifying the acetylated globin by acid precipitation, filtration and redissolution in alkaline water up to an acetylated globin content of from 2.5% to 10% by weight;

(f) reacting the purified acetylated globin with an aqueous solution of an iron compound selected from the group consisting of ferric chloride, iron saccharate and iron fructate for a time of from 1 to 3 hours, at room temperature;

(g) purifying the reaction product by acid precipitation and alkaline redissolution;

(h) recovering the product by lyophilizing the obtained aqueous solution.

5. A process for the preparation of bio-available iron-protein derivatives according to claim 4 wherein the weight ratio between the acetylated globin and the iron content of ferric chloride or iron saccharate or iron fructate in stage (f) is of from 49:1 to 4:1.

6. A process for the preparation of bio-available iron-protein derivatives according to claim 4 wherein the reaction product of ferric chloride with fructose or sucrose is obtained by reacting ferric chloride and fructose or sucrose in an aqueous medium, at room temperature and in alkaline conditions, the weight ratio between iron and sucrose or fructose being of from 2:5 to 1:20.

7. A process for the preparation of bio-available iron-protein derivatives according to claim 4 wherein the iron content of saccharate or fructate is 10% by weight.

8. A process for the preparation of bio-available iron-protein derivatives according to claim 5 wherein the iron compound is ferric chloride and the weight ratio between acetylated globin and iron is of from 49:1 to 15:1.

9. A process for the preparation of bio-available iron-protein derivatives according to claim 5 wherein the iron compound is iron saccharate, or iron fructate and the weight ratio between acetylated globin and iron is of from 19:1 to 4:1.

10. A pharmaceutical composition for treating and preventing iron deficiency in animals and humans, containing as active principle an effective amount of a bio-available iron-protein derivative containing of from 2 to 20% by weight of iron and of from 12 to 16% of nitrogen and obtained by reacting acetylated globin with an iron compound selected from the group consisting of ferric chloride, iron fructate and iron saccharate in admixture with the usual pharmaceutically acceptable additives.

* * * * *